US009132507B2

(12) United States Patent
Takiguchi et al.

(10) Patent No.: US 9,132,507 B2
(45) Date of Patent: Sep. 15, 2015

(54) LASER WELDING METHOD AND LASER WELDED MEMBER FOR ENDOSCOPE

(71) Applicant: Olympus Corporation, Tokyo (JP)

(72) Inventors: Kinji Takiguchi, Tokyo (JP); Takeshi Hidaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 345 days.

(21) Appl. No.: 13/889,703

(22) Filed: May 8, 2013

(65) Prior Publication Data

US 2013/0240493 A1 Sep. 19, 2013

Related U.S. Application Data

(63) Continuation of application No. PCT/JP2011/075730, filed on Nov. 8, 2011.

(30) Foreign Application Priority Data

Nov. 17, 2010 (JP) ................................. 2010-256690

(51) Int. Cl.
*A61B 1/00* (2006.01)
*B23K 26/32* (2014.01)
(Continued)

(52) U.S. Cl.
CPC ............... *B23K 26/20* (2013.01); *A61B 1/0011* (2013.01); *A61B 1/00071* (2013.01);
(Continued)

(58) Field of Classification Search
CPC .. A61B 1/00064; A61B 1/0011; B23K 26/20; B23K 26/32; B23K 26/3206; B23K 31/00; B23K 31/003

USPC ............... 600/101, 138; 428/592; 219/121.64
See application file for complete search history.

(56) References Cited

U.S. PATENT DOCUMENTS 5,746,696 A * 5/1998 Kondo .......................... 600/139
2009/0160112 A1* 6/2009 Ostrovsky ..................... 267/155

FOREIGN PATENT DOCUMENTS

JP          60-246741 A    12/1985
JP           5-161597 A     6/1993
(Continued)

OTHER PUBLICATIONS

Zhang Wei-Zhe; "Research on Stainless Steel 304 Sheet Laser Welding Technique"; Dalian University of Technology, Nov. 1, 2009, pp. 30-31. (Partial English translation of First Notice of Rejection Grounds (p. 3, line 23-26 of main text of First Notice of Rejection Grounds for the corresponding Chinese patent application No. 201180054439.7).

(Continued)

*Primary Examiner* — Samuel M Heinrich
(74) *Attorney, Agent, or Firm* — Arent Fox LLP

(57) ABSTRACT

In a laser welding method for an endoscope, when the thickness of the plate of an outer cylindrical member is set as h, the thickness of the plate of an inner coil-shaped member is set as $h_c$, the maximum welding energy of laser welding that does not change the inner and outer diameters of the outer cylindrical member in the place where the inner coil-shaped member is not placed inside the outer cylindrical member is set as $E_1$, and the minimum welding energy that enables the outer cylindrical member to be fixed by welding to the inner coil-shaped member is set as $E_2$, the spiral weld beads do not overlap, the welding depth H from the outer cylindrical member to the inner coil-shaped member holds true $h<H<h+h_c$, the welding energy E satisfies the expression of $E_2 \leq E \leq E_1$.

2 Claims, 9 Drawing Sheets

(51) Int. Cl.
  *B23K 31/00* (2006.01)
  *B23K 26/20* (2014.01)
  *B23K 26/067* (2006.01)
  *B23K 26/30* (2014.01)

(52) U.S. Cl.
  CPC .......... *B23K 26/0676* (2013.01); *B23K 26/305* (2013.01); *B23K 26/32* (2013.01); *B23K 26/3206* (2013.01); *B23K 31/00* (2013.01); *B23K 31/003* (2013.01)

(56) References Cited

FOREIGN PATENT DOCUMENTS

| JP | 6-16790 B2 | 3/1994 |
| JP | H08-5934 A | 1/1996 |
| JP | 2000-70221 A | 3/2000 |
| JP | 2001-001173 A | 1/2001 |
| JP | 2008-238193 A | 10/2008 |
| JP | 2009-154194 A | 7/2009 |

OTHER PUBLICATIONS

First Notice of Rejection Grounds (issued by Chinese Patent Office) for the corresponding Chinese patent application No. 201180054439.7 (Partial English translation attached), Jun. 2015.
International Search Report for Appl. No. PCT/JP2011/075730, dated Feb. 14, 2012.
Decision of Rejection issued by the JPO for counterpart application No. JP 2010-256690, date of mailing Feb. 24, 2015 (Partial English translation attached).
Japanese Notice of Rejection Grounds (for corresponding Japanese Patent Application No. 2010-256690, issue date Jul. 15, 2014 (Partial English translation).
Zhang Wei-Zhe; "Research on Stainless Steel 304 Sheet Laser Welding Technique"; University of Technology, Nov. 1, 2009, pp. 30-31. (Partial English translation of First Notice of Rejection Grounds (p. 3, line 23-26 of main text of First Notice of Rejection Grounds for the corresponding Chinese patent application No. 201180054439.7).
First Notice of Rejection Grounds (issued by Chinese Patent Office) for the corresponding Chinese patent application No. 201180054439.7 (Partial English translation attached), Jun. 2014.

\* cited by examiner

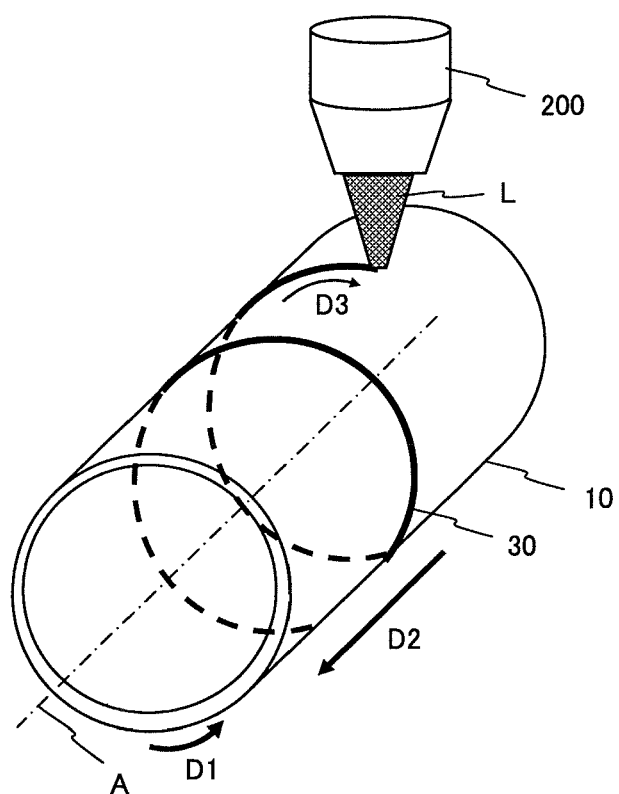
F I G. 2

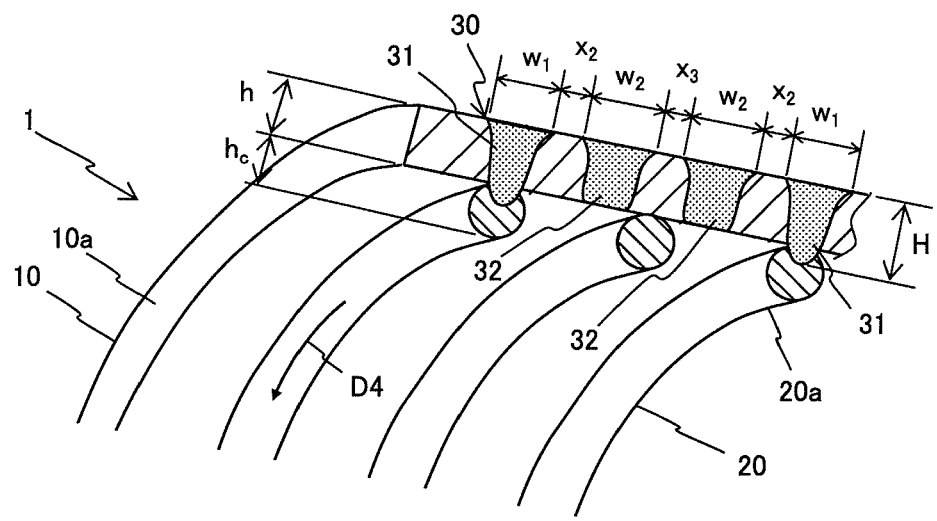
F I G. 3 C

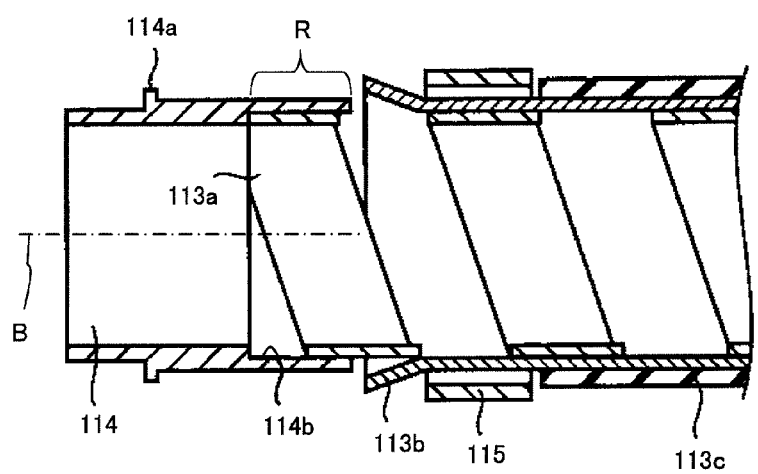
F I G. 5

LASER WELDING METHOD AND LASER WELDED MEMBER FOR ENDOSCOPE

CROSS REFERENCE TO RELATED APPLICATIONS

This is Continuation application of PCT application No. PCT/JP/2011/075730 filed Nov. 8, 2011, which was not published under PCT Article 21 (2) in English.

This application is based upon and claims the benefit of priority from the prior Japanese Patent Application No. 2010-256690, filed Nov. 17, 2010, the entire contents of which are incorporated herein by reference.

BACKGROUND OF THE INVENTION

The present invention relates to: a laser welding method for an endoscope for fixing by welding the outer cylindrical member of an endoscope to the inner coil-shaped member positioned inside the outer cylindrical member by irradiating the outer cylindrical member with laser beams from the periphery; and a laser welded member for an endoscope provided with the outer cylindrical member and the inner coil-shaped member fixed by welding to each other in the laser welding method for an endoscope.

DESCRIPTION OF THE RELATED ART

Conventionally, when a coil-shaped member is joined to the inner surface of the pipe-shaped member of an endoscope as inscribed in the pipe-shaped member, it is a well-known technique to deformation-process the pipe-shaped member in the direction in which the pipe-shaped member is diameter reduced in the method such as so-called swaging etc. for processing the outer diameter of the pipe-shaped member from the outside of the pipe-shaped member, and then weld the deformation-processed part by laser beams (for example, refer to the Patent Document 1).

The Patent Document 1 describes the method of performing laser welding with a metal foil interposed between a pipe-shaped member and a coil-shaped member, and a technique of shaping by shaving the periphery of the weld part after the laser welding.

Furthermore, as a method of welding using laser beams, it is a well-known method of welding by irradiating a pipe-shaped member with laser beams from the periphery of the pipe-shaped member along the periphery (for example, refer to Patent Documents 2 and 3).

Patent Document 1: Japanese Examined Patent Application Publication No. 6-16790
Patent Document 2: Japanese Laid-open Patent Publication No. 5-161597
Patent Document 3: Japanese Laid-open Patent Publication No. 60-246741

SUMMARY OF THE INVENTION

The laser welding method for an endoscope fixes by welding an outer cylindrical member of an endoscope to an inner coil-shaped member positioned inside the outer cylindrical member by irradiating the outer cylindrical member with laser beams from the periphery of the outer cylindrical member spirally on the axis of the outer cylindrical member. When the thickness of the plate of the outer cylindrical member is set as h, the thickness of the plate of the inner coil-shaped member is set as $h_c$, the maximum welding energy of laser welding that does not change the inner and outer diameters of the outer cylindrical member in the place where the inner coil-shaped member is not placed inside the outer cylindrical member is set as $E_1$, and the minimum welding energy that enables the outer cylindrical member to be fixed by welding to the inner coil-shaped member is set as $E_2$, the spiral weld beads formed by the irradiating of the outer cylindrical member do not overlap, the welding depth H from the outer cylindrical member to the inner coil-shaped member holds true $h < H < h + h_c$, the welding energy E when the welding depth of the fixing by welding between the outer cylindrical member and the inner coil-shaped member is H satisfies the expression of $E_2 \leq E \leq E_1$.

BRIEF DESCRIPTION OF THE DRAWINGS

FIG. 2 is a rough perspective view of a pipe-shaped member (an outer cylindrical member) for explanation of the laser welding method for an endoscope according to an embodiment of the present invention;

FIG. 3C is a partial sectional view (3) of a welding region for explanation of the laser welding method for an endoscope according to an embodiment of the present invention;

FIG. 5 is a sectional view of a hose connection unit to which the laser welding method for an endoscope according to an embodiment of the present invention is applied.

DESCRIPTION OF THE PREFERRED EMBODIMENT

If the deformation processing such as swaging as described in the patent document 1 above is identified, the pipe-shaped member and the coil-shaped member are deformed, thereby changing the inner and outer diameters of the pipe-shaped member and the coil-shaped member.

Therefore, although an endoscope used by inserting a treatment tool into the coil-shaped member is to be designed with the deformation by the swaging taken into account, the swaging increases the variance in dimensions after the deformation. Accordingly, with a member having a small diameter such as a pipe-shaped member for an endoscope, it is difficult to manage the inner and outer diameters of welded parts with high accuracy.

In addition, when the welding is performed by irradiating the pipe-shaped member along the periphery with laser beams as described in the patent documents 2 and 3, weld beads overlap with one another and generate uneven depth, thereby failing in unsatisfactory laser welding.

The laser welding method for an endoscope and the laser welded member for an endoscope according to the embodiments of the present invention are described below with reference to the attached drawings.

Figure 1:
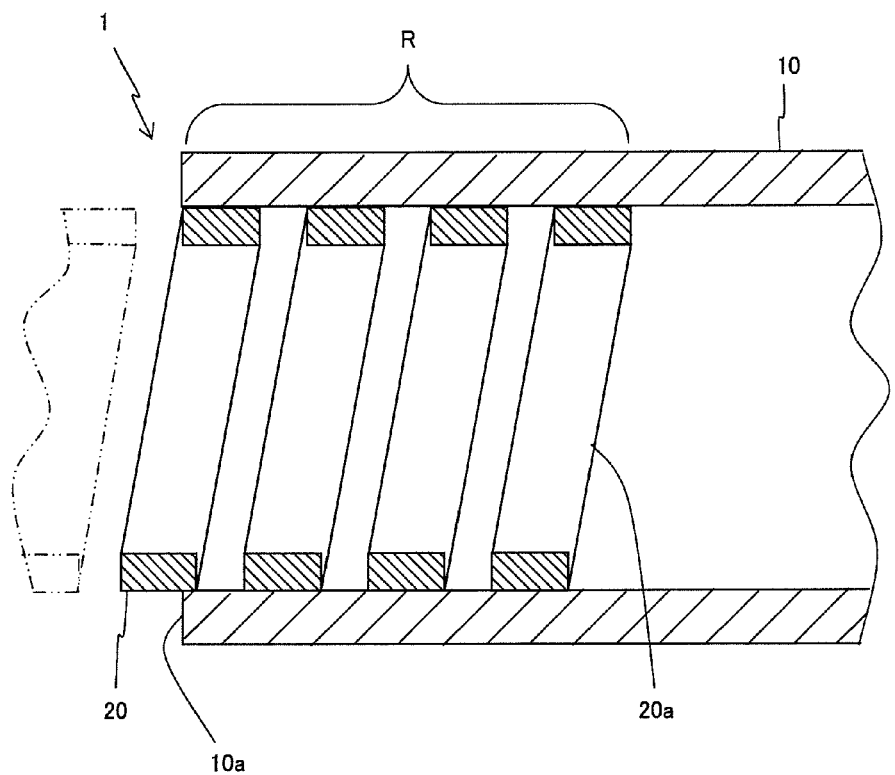
FIG. 1 is a rough sectional view of the laser welded member for an endoscope according to an embodiment of the present invention.

FIG. 1 is a rough sectional view of the laser welded member 1 according to an embodiment of the present invention.

FIG. 2 is a rough perspective view of the pipe-shaped member for explanation of the laser welding method for an endoscope according to an embodiment of the present invention.

FIGS. 3A through 3D are partial sectional views of a welding region R for explanation of the laser welding method described above.

As illustrated in FIG. 1, a laser welded member 1 is an example of an outer cylindrical member. For example, the laser welded member 1 includes, for example, a metal pipe-shaped member 10 and an example of an inner coil-shaped member positioned inside the pipe-shaped member 10, for example, a coil-shaped member 20 having a rectangular section.

The pipe-shaped member 10 and the coil-shaped member 20 are substantially cylindrical. A part of the coil-shaped member 20 on an end part 20a side fits the inner surface of a part of the pipe-shaped member 10 on an end part 10a side. The pipe-shaped member 10 and the coil-shaped member 20 are fixed by welding by the laser beam L irradiated by a laser beam irradiation device 200 illustrated in FIG. 2. A weld part 30 as examples of spiral weld beads is formed by irradiating a welding region R illustrated in FIG. 1 with the laser beam L as, for example, a YAG laser from the periphery of the pipe-shaped member 10.

As illustrated in FIG. 2, the fitted pipe-shaped member 10 and coil-shaped member 20 rotates in the direction D1 of rotation and are fed in the direction D2 of feed with both members held by a holding device not illustrated in the attached drawings. The laser beam irradiation device 200 irradiates the pipe-shaped member 10 and coil-shaped member 20 in the state above with the laser beam L.

Relating to the direction D1 of rotation and the direction D2 of feed, for example, the laser beam irradiation device 200 may be moved in the direction D2 of feed because the pipe-shaped member 10 and the coil-shaped member 20 may rotate or move relative to the laser beam irradiation device 200.

As illustrated in FIG. 2, the weld part 30 which is welded by laser beam L is continuously irradiated with the laser beam L from the periphery spirally on the axis (central axis) of the pipe-shaped member 10. Although the laser beam L may be intermittently applied, it may be continuously applied to for, the weld part 30 with high accuracy.

Figure 3A:
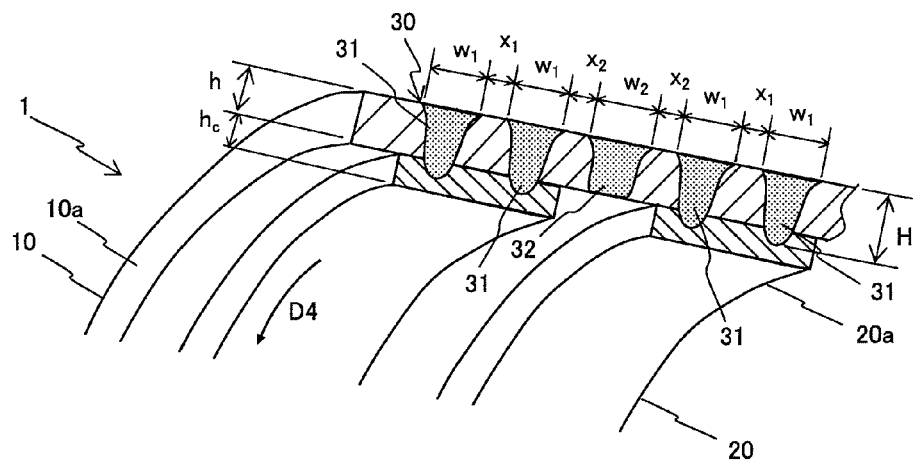
FIG. 3A is a partial sectional view (1) of a welding region for explanation of the laser welding method for an endoscope according to an embodiment of the present invention.

As illustrated in FIG. 3A, the coil-shaped member 20 positioned inside the pipe-shaped member 10 is an application example of a coil-shaped member in which panel coils do not contact tightly. The weld part 30 is irradiated with the laser beam L of the same laser irradiation condition between the parts (weld parts 31) on the periphery of the pipe-shaped member 10 having the coil-shaped member 20 positioned inside and another part (weld parts 32). The laser irradiation condition may be, for example, a wavelength, an optical output, a spot diameter, an oscillation pulse width, a moving speed, etc.

First in the embodiment of the present invention, the weld part 32 which has not the coil-shaped member 20 inside is set under the condition that the inner and outer diameters of the pipe-shaped member 10 are not changed by the adjustment of the laser irradiation condition. In this case, the width of the weld part 32 is $w_2$.

In the laser irradiation condition above, the width of the weld beads of the weld part 31 having the coil-shaped member 20 inside is $w_1$. The moving speed and the feed speed are controlled so the weld parts 30 do not overlap, and the clearance $x_1$ and $x_2$ between the weld parts 30 (31 and 32) are set so that the expression $x_1, x_2 > 0$ holds true.

If the thickness of the plate of the pipe-shaped member 10 is h, the thickness of the plate of the coil-shaped member 20 is $h_c$, the maximum welding energy of the laser welding in which the inner and outer diameters of the pipe-shaped member 10 are not changed in the place where the coil-shaped member 20 is not positioned inside the pipe-shaped member 10 is $E_1$, and the minimum welding energy which enables the pipe-shaped member 10 and the coil-shaped member 20 to be fixed by welding is $E_2$, then the welding energy E with the weld parts 31 and 32 formed spiral on the axis of the pipe-shaped member 10, with the weld parts 31 and 32 not overlapping each other, with the welding depth H from the pipe-shaped member 10 to the coil-shaped member 20 set as $h < H < h + h_c$, and with the welding depth (melting depth) set as H satisfies the expression $E_2 \leq E \leq E_1$.

The maximum welding energy $E_1$ of the laser welding in which the inner and outer diameters of the pipe-shaped member 10 are not changed in the place where the coil-shaped member 20 is not positioned inside the pipe-shaped member 10 is the maximum value of the welding energy which generates only a change smaller than 1% of the diameters of inner and outer diameters of the pipe-shaped member 10. In the present embodiment, the welding energy which does not generate a change of the inner and outer diameters of the pipe-shaped member 10 in the place where the coil-shaped member 20 is not positioned inside the pipe-shaped member 10 does not change the inner and outer diameters of the coil-shaped member 20 in the place where the coil-shaped member 20 is positioned inside the pipe-shaped member 10 (only a change of 1% or lower of the diameter is generated).

Since the welding energy E is expressed by "welding energy per unit time×welding time", the welding time and also the welding energy E may be easily adjusted by the feeding speed etc. in the direction D2 of feed although the intensity of the laser beam L is constant. However, it is requested that the speed in the direction D1 of rotation and the direction D2 of feed, the intensity of laser beams, etc. are adjusted so that the weld parts 30 do not overlap one another.

The direction D3 of rotation illustrated in FIG. 2 as the direction of forming the weld part 30 may be the same direction of spiral rotation of the coil-shaped member 20 illustrated in FIG. 3A. The weld part 30 may be formed with high accuracy while protecting against uneven welding depth etc. by forming the clearance $x_1$ and $x_2$ so that the weld parts 30 do not overlap on the peripheral surface of the pipe-shaped member 10. The width $w_1$ of the weld part 31 is smaller than the width $w_2$ of the weld part 32, and the laser irradiation condition is constant. Therefore, the clearance $x_1$ between the weld parts 31 is larger than the clearance $x_2$ between the weld parts 31 and 32.

Figure 3B:
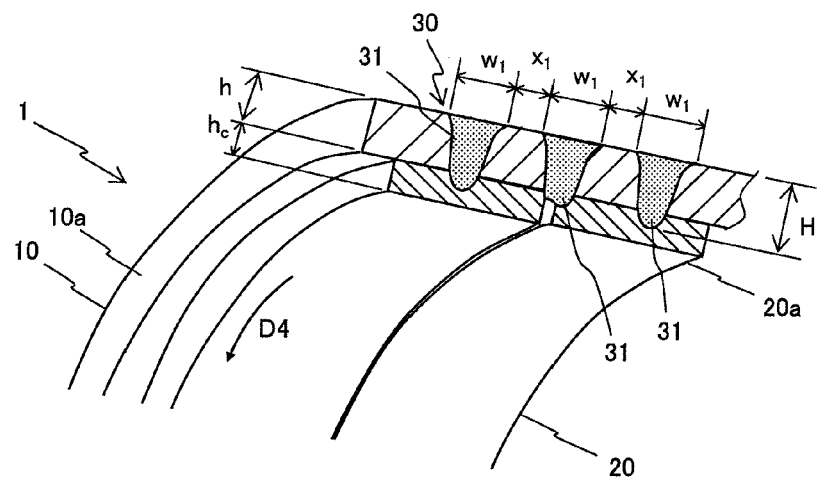
FIG. 3B is a partial sectional view (2) of a welding region for explanation of the laser welding method for an endoscope according to an embodiment of the present invention.

As illustrated in FIG. 3B, the coil-shaped member 20 positioned inside the pipe-shaped member 10 may be configured so that the coils are close to each other using panel coils. The weld part 30 is configured by the weld part 31 only in which the coil-shaped member 20 is positioned inside the pipe-shaped member 10. Also in this case, the clearance $x_1$ between the weld parts 31 is set as $x_1 > 0$.

Also as illustrated in FIG. 3C, the coil-shaped member 20 may be configured so that the coils having a circular section are not tightly close to each other. As illustrated in FIG. 3C, the clearance $x_2$ between the weld parts 31 and 32 and the clearance $x_3$ between the weld parts 32 also satisfy the expression $x_2, x_3 > 0$.

Figure 3D:
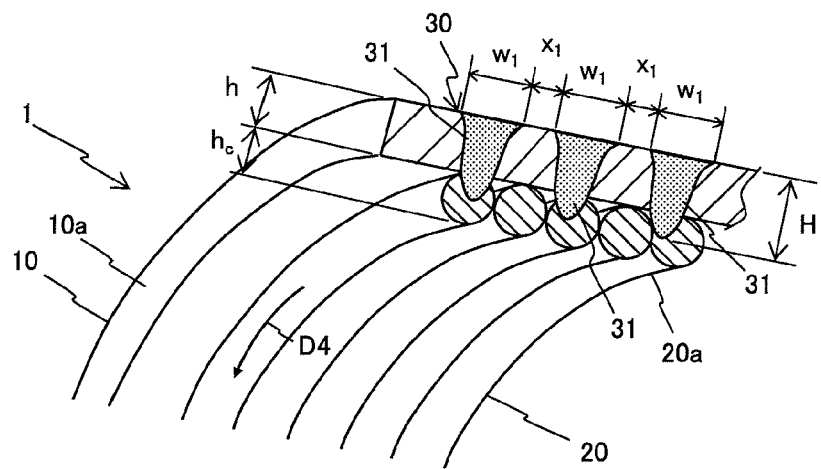
FIG. 3D is a partial sectional view (4) of a welding region for explanation of the laser welding method for an endoscope according to an embodiment of the present invention.

As illustrated in FIG. 3D, the coil-shaped member 20 may be configured by coils having a circular section and close to each other. In this case, the weld part 30 is configured by the weld parts 31 only with the coil-shaped member 20 positioned inside the pipe-shaped member 10, and the clearance $x_1$ satisfies the expression $x_1>0$.

In attached drawings for the present embodiment, the weld part 30 makes several rotations along the periphery of the pipe-shaped member 10, but it may also be designed so that the weld part 30 makes several tens of rotations, several hundreds of rotations, or even more depending on the size of a target welding region R, the necessary intensity of the target welding region R, the type of laser beam L, etc.

The present embodiment also describes an example of using the coil-shaped member 20 having a rectangular or circular section as an inner coil-shaped member, but the inner coil-shaped member may have other shapes of section so far as the inner coil-shaped member may be welded to the outer cylindrical member. Also the outer cylindrical member may have another design such as a polygonal pipe etc.

Furthermore, the pipe-shaped member 10 and the coil-shaped member 20 may be swaged from the periphery of the pipe-shaped member 10 (deformation processing), or a member for joining such as metal foil etc. may be interposed between the pipe-shaped member 10 and the coil-shaped member 20, and then the laser beams may be applied as described above.

According to the present embodiment, the pipe-shaped member 10 is irradiated with laser beams from the periphery spirally on the axis A of the pipe-shaped member 10 so that the laser beams do not overlap one another. Therefore, it is not necessary to perform deformation processing for joining the pipe-shaped member 10 and the coil-shaped member 20 before laser irradiation. Furthermore, when a member for joining between the pipe-shaped member 10 and the coil-shaped member 20 is not interposed, or when the coil-shaped member 20 is not positioned inside the pipe-shaped member 10, the laser welding may be correctly performed without changing the inner and outer diameters of the pipe-shaped member 10. Furthermore, the laser welding may be performed in a short time with a simple configuration in a large welding region R.

Also in the present embodiment, the laser beam L is continuously irradiated spirally on the axis A of the pipe-shaped member 10. Therefore, the dimension accuracy of the pipe-shaped member 10 and the coil-shaped member 20 may be maintained, thereby performing the laser welding with higher accuracy.

Furthermore, according to the present embodiment, the coil-shaped member 20 is used as an inner coil-shaped member, and the laser beam L is applied spirally in the same spiral direction between the spiral (direction D4 of spiral) of the coil-shaped member 20 and the direction D3 of rotation (direction of forming the weld part 30). Therefore, the laser beam L may be easily irradiated at the position where the coil-shaped member 20 is positioned inside the periphery of the pipe-shaped member 10, and the laser welding may be performed with higher accuracy.

Figure 4:
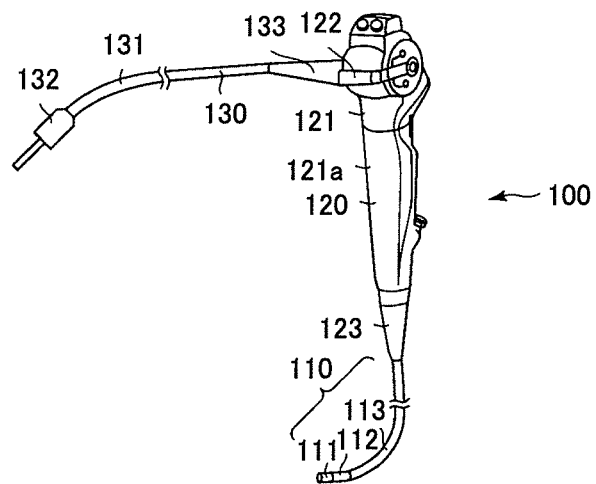
FIG. 4 is a perspective view of an endoscope to which the laser welding method for an endoscope according to an embodiment of the present invention is applied.

FIG. 4 is a perspective view of an endoscope 100 to which the laser welding method according to the present embodiment is applied.

FIG. 5 is a sectional view of the hose connection unit of the endoscope.

As illustrated in FIG. 4, the endoscope 100 includes an insertion unit 110 to be inserted into a very narrow space, an operation unit 120 arranged at the base end unit of the insertion unit 110, and a universal cable 130 extended from the operation unit 120.

The insertion unit 110 includes a hard end unit 111, a curved unit 112 arranged at the base end unit of the hard end unit 111, and a hose (flexible tube) 113 arranged at the base end unit of the curved unit 112.

The operation unit 120 includes a body 121 of the operation unit having a gripper 121a, a curved operation knob 122 arranged at the body 121 of the operation unit, and an anti-fold unit 123 arranged at the base end unit of the hose 113 and arranged at the gripper 121a of the body 121 of the operation unit.

The universal cable 130 includes a flexible pipe 131 extended from the body 121 of the operation unit, a connector 132 arranged at the end part of the flexible pipe 131 farther from the body 121 of the operation unit, and an anti-fold unit 133 arranged at the end part of the flexible pipe 131 closer to the body 121 of the operation unit.

The hose 113 includes a flex 113a as an example of an inner coil-shaped member, a blade 113b arranged outside the flex 113a, and a shell 113c arranged outside the blade 113b.

The flex 113a is substantially cylindrical by spirally forming a belt-shaped thin plate material such as stainless steel. The tip of the flex 113a is cut so that it makes 90 degrees with respect to the central axis in the longitudinal direction of the flex 113a.

The blade 113b is substantially cylindrical and formed by, for example, twisting bundles of wires of stainless steel.

The shell 113c is substantially cylindrical and formed by covering the outside of the blade 113b with a flexible resin material such as a rubber material etc.

The connection cap 114 is substantially cylindrical formed by a metal material etc. such as a stainless steel material etc. On the connection cap 114, a flange unit 114a is formed as extended outward along the diameter. On the inner circumference of the connection cap 114, a concave part 114b is formed so that the diameter of the part is larger than the diameter of the tip part of the connection cap 114.

The inner diameter of the concave part 114b of the connection cap 114 is equal to or smaller than the outer diameter of the flex 113a so that the peripheral surface of the flex 113a may be closely fitted to the inner surface of the concave part 114b when the flex 113a is place in a natural state (in which no external force is applied).

As described above, since the tip of the flex 113a is cut to make approximately 90 degrees with respect to the direction of the axis, the tip of the flex 113a touches the step part of the tipoff the concave part 114b while energizing the peripheral surface of the flex 113a to the inner surface of the concave part 114b of the connection cap 114. That is, the tip of the flex 113a is positioned by and fitted to the concave part 114b of the connection cap 114.

The connection cap 114 as an example of the thus fitted outer cylindrical member and the flex 113a as an example of the inner coil-shaped member are spirally fixed by welding on the axis (central axis) B of the connection cap 114 in the welding region R like the laser welding between the pipe-shaped member 10 (outer cylindrical member) and the coil-shaped member (inner coil-shaped member) 20 as explained above with reference to FIGS. 1 through 3D.

A caulking member 115 arranged outside the blade 113b is formed by a metal material such as a stainless steel etc. The caulking member 115 is used outside the connection cap 114 (deformation processing) at the tip side of the blade 113b which touches the flange unit 114a of the connection cap 114. Afterwards, the above-mentioned laser welding according to the present embodiment may be performed. The laser welding according to the present embodiment is applicable to the welding of the coil-shaped hose 113 (flex 113a), and other parts may be defined as a welding region R.

Although the connection cap 114 and the flex 113a may be fixed by welding after caulking the connection cap 114 to the outside of the flex 113a, it is more preferable not to use a caulking configuration to avoid a deformation because the above-mentioned laser welding may fix the connection cap 114 and the flex 113a without fail.

Figure 6:
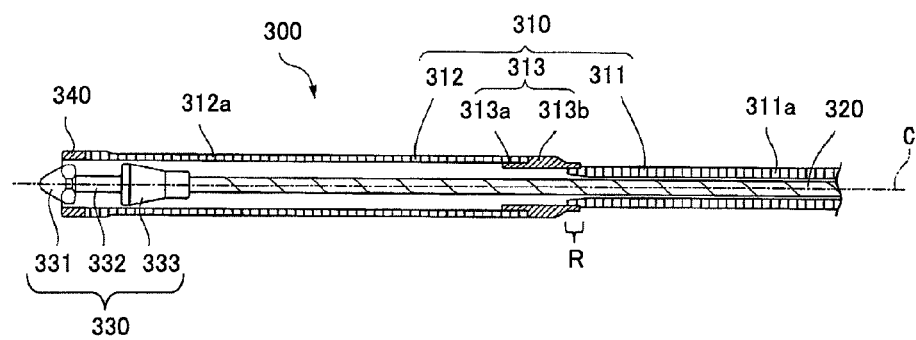
FIG. 6 is a sectional view of the relevant part of the clip device for an endoscope (treatment tool for an endoscope) according to an embodiment of the present invention.

FIG. 6 is a sectional view of the important part and illustrates a clip device 300 for an endoscope to which the laser welding method according to the present embodiment is applied.

As illustrated in FIG. 6, the clip device 300 for an endoscope as an example of a treatment tool for an endoscope is inserted into, for example, a treatment tool insertion channel of an endoscope insertion unit not illustrated in the attached drawings, and is used with an endoscope. Therefore, the insertion unit configured by a pipe-shaped substance 310, an operation wire 320, etc. is formed as sufficiently longer than the treatment tool insertion channel. The insertion unit is flexible for a curve dependent of the curve of the endoscope insertion unit.

The operation wire 320 is arranged as extending along the pipe-shaped substance 310 and freely fed forward and backward with respect to the pipe-shaped substance 310. Furthermore, connected to the tip of the operation wire 320 is a hook 330 having the diameter larger than the diameter of the base end unit to which a clip unit not illustrated in the attached drawings is engaged as freely attached and detached.

The hook 330 is used to hang the clip unit not illustrated in the attached drawings. In addition, the hook 330 is formed by a metal material such as a stainless steel material etc., and includes a substantially conical engagement unit 331 for hanging and engaging the clip unit, and a wire connection unit 333 for connection of the engagement unit 331 to the operation wire 320 by, for example, welding through an axis unit 332.

The pipe-shaped substance 310 includes a near coil 311 arranged at the base end side, a far coil 312 having an inner diameter larger than the inner diameter of the near coil 311, and a coil connection pipe 313 for connection of the near coil 311 to the far coil 312. The coil connection pipe 313 is harder than the near coil 311 and the far coil 312.

The near coil 311 is cylindrically formed by closely and spirally winding a flat line 311a obtained by squeezing a circle-section line of, for example, a stainless steel material into a flat line.

The far coil 312 is cylindrically formed by closely and spirally winding a flat line 312a of a substantially rectangular section of, for example, a stainless steel material.

At the tip of the far coil 312, an end tip 340 of, for example, a stainless steel formed circularly.

The coil connection pipe 313 is, for example, a substantially pipe-shaped stainless steel material. The coil connection pipe 313 includes a far connection unit 313a having a substantially the same outer diameter as the inner diameter of the far coil 312, and a near connection unit 313b which is connected to the far connection unit 313a and has substantially the same outer diameter as the near coil 311. The inner diameter of the far connection unit 313a is substantially the same as the inner diameter of the near connection unit 313b.

The coil connection pipe 313 (near connection unit 313b) functions as an example of the outer cylindrical member, and the near coil 311 functions as an example of an inner coil-shaped member positioned inside the coil connection pipe 313.

The coil connection pipe 313 and the near coil 311 are spirally laser welded on the axis (central axis) C of the coil connection pipe 313 in the welding region R as with the laser welding between the pipe-shaped member 10 (outer cylindrical member) and the coil-shaped member (inner coil-shaped member) 20 described above with reference to FIGS. 1 through 3D.

If laser beams may be applied from the outside of the far coil 312, the far coil 312 is used as an outer cylindrical member, and the coil connection pipe 313 (far connection unit 313a) is used as an inner coil-shaped member, thereby performing the laser welding method. The laser welding according to the present embodiment is applicable to the welding of the coil-shaped near coil 311 etc. However, other parts may be used as welding regions.

For example, the connection part between the engagement unit 331 of the hook 330 and the operation wire 320, or other connection parts may be processed by the laser welding according to the present embodiment.

In the explanation above, the endoscope 100 (FIGS. 4 and 5) provided with outer cylindrical member and the inner coil-shaped member which are fixed by welding by the above-mentioned laser welding method, and the clip device 300 for an endoscope (FIG. 6) as an example of a treatment tool for an endoscope are described as preferable application examples according to the present embodiment. That is, the laser welding method according to the present embodiment is applicable so far as the welding is performed between an outer cylindrical member of an endoscope and an inner coil-shaped member.

What is claimed is:

1. A laser welding method for an endoscope fixes by welding an outer cylindrical member of an endoscope to an inner coil-shaped member positioned inside the outer cylindrical member by irradiating the outer cylindrical member with laser beams from a periphery of the outer cylindrical member spirally on an axis of the outer cylindrical member, the method comprising:

when a thickness of a plate of the outer cylindrical member is set as h, a thickness of a plate of the inner coil-shaped member is set as $h_c$, a maximum welding energy of laser welding that does not change inner and outer diameters of the outer cylindrical member in a place where the inner coil-shaped member is not placed inside the outer cylindrical member is set as $E_1$, and the minimum welding energy that enables the outer cylindrical member to be fixed by welding to the inner coil-shaped member is set as $E_2$, spiral weld beads formed by the irradiating of the outer cylindrical member do not overlap;

a welding depth H from the outer cylindrical member to the inner coil-shaped member holds true $h<H<h+h_c$; and the welding energy E when the welding depth of the fixing by welding between the outer cylindrical member and the inner coil-shaped member is H satisfies an expression of $E_2 \leq E \leq E_1$.

2. A laser welded member for an endoscope in the method according to claim 1, comprising the outer cylindrical member and the inner coil-shaped member fixed by welding to each other.

* * * * *